United States Patent [19]
Underwood et al.

[11] Patent Number: 5,397,582
[45] Date of Patent: * Mar. 14, 1995

[54] FLAVORING AND BROWNING MATERIALS BY PYROLYSIS OF SUGARS AND STARCHES

[75] Inventors: Gary L. Underwood; John A. Stradal, both of Manitowoc, Wis.

[73] Assignee: Red Arrow Products Company Inc., Manitowoc, Wis.

[*] Notice: The portion of the term of this patent subsequent to Mar. 8, 2011 has been disclaimed.

[21] Appl. No.: 112,946

[22] Filed: Aug. 30, 1993

Related U.S. Application Data

[63] Continuation-in-part of Ser. No. 674,442, Mar. 27, 1991, Pat. No. 5,292,541, which is a continuation-in-part of Ser. No. 535,735, Jun. 8, 1990, abandoned, Ser. No. 498,849, Mar. 26, 1990, abandoned, Ser. No. 416,963, Oct. 4, 1989, Pat. No. 5,039,537, and Ser. No. 358,650, May 26, 1989, Pat. No. 4,994,297.

[51] Int. Cl.⁶ .............................................. A23L 1/03
[52] U.S. Cl. ................................... 426/250; 426/271; 426/431; 426/540; 426/652; 426/655
[58] Field of Search ............... 426/650, 655, 520, 524, 426/431, 314, 315, 534, 652, 250, 540, 235, 271

[56] References Cited

U.S. PATENT DOCUMENTS

| | | |
|---|---|---|
| 3,106,473 | 10/1963 | Hollenbeck . |
| 3,330,669 | 7/1967 | Hollenbeck . |
| 3,505,407 | 4/1970 | Cavitt . |
| 3,618,588 | 11/1971 | Anwar et al. . |
| 3,806,609 | 4/1974 | Goblik et al. . |
| 4,218,487 | 8/1980 | Jaeggi . |
| 4,359,481 | 11/1982 | Smits et al. . |
| 4,431,032 | 2/1984 | Nicholson . |
| 4,431,033 | 2/1984 | Nicholson . |
| 4,496,595 | 1/1985 | Nicholson . |
| 4,504,500 | 3/1985 | Schneck et al. . |
| 4,504,501 | 3/1985 | Nicholson . |
| 4,504,507 | 3/1985 | Nicholson . |
| 4,505,939 | 3/1985 | Chiu . |
| 4,525,397 | 6/1985 | Chiu . |
| 4,614,662 | 1/1986 | Ramaswamy et al. . |
| 4,657,765 | 4/1987 | Nicholson et al. . |
| 4,717,576 | 6/1988 | Nicholson et al. . |
| 4,876,108 | 10/1989 | Underwood et al. . |
| 4,883,676 | 11/1989 | Sophianopoulos et al. . |
| 4,938,868 | 7/1990 | Nelson . |
| 4,973,485 | 11/1990 | Rich . |
| 4,994,297 | 2/1991 | Underwood et al. . |

FOREIGN PATENT DOCUMENTS

| | | |
|---|---|---|
| 932686 | 8/1973 | Canada . |
| 1137637 | 12/1968 | United Kingdom . |
| WO88/00935 | 2/1988 | WIPO . |

OTHER PUBLICATIONS

Arseneu et al., "A Study of Reaction Mechanisms by DSC and TG," *Thermal Analysis*, vol. 3, Proceedings Third ICTA Davos, 1971, pp. 319–326.

Bailey, "Inhibition of Warmed-Over Flavor, With Emphasis on Maillard Reaction Products", *Food Technology*, Jun. 1988, pp. 123–126.

Beaumont et al. "Influence of Physical and Chemical Parameters on Wood Pyrolysis," *Ind. Eng. Chem. Process Des. Dev.*, vol. 23, No. 4, 1984, pp. 637–641.

Berg et al., "Characterization of Solids Mixing in an Ultra-Rapid Fluidized Reactor," Paper presented in London, Ontario, Canada, May 12–15, 1986.

Berg et al., "Rapid Mixing Studies Between Transported Solids in an Ultra-Rapid Fluidized Reactor," Powder & Bulk Solids Conference, Rosemont, Ill., May, 1985.

(List continued on next page.)

*Primary Examiner*—Donald E. Czaja
*Assistant Examiner*—Anthony Weier
*Attorney, Agent, or Firm*—Marshall, O'Toole, Gerstein, Murray & Borun

[57] ABSTRACT

A method of producing a browning liquid product by pyrolyzing sugars and starches. The browning liquid imparts a brown, smoked color to a cooked foodstuff without imparting an undesirable strong smoked flavor to the foodstuff.

31 Claims, 3 Drawing Sheets

OTHER PUBLICATIONS

Byrne et al., "The Pyrolysis of Cellulose and the Action of Flame Retardants," *J. Appl. Chem.*, vol. 16, Mar. 1966, pp. 81–88.

Collins et al., "Nuclear Magnetic Resonance Spectra of Glycolaldehyde," *J. Chem. Soc. (B)*, 1971, pp. 1352–1355.

Evans et al., "New Approaches to the Study of Cellulose Pyrolysis," *American Chemical Society*, vol. 36, No. 2, 1991, pp. 714–724.

Fenton et al., "Crystalline Glycollic Aldehyde," University of Chemical Laboratory, Cambridge.

Glassner et al. "Gas Chromotographic Analysis of Products from Controlled Application of Heat to Paper and Levoglucosan," *Analytical Chemistry*, vol. 37, No. 4, Apr., 1965, pp. 525–527.

Graham et al., "Fast Pyrolysis of Biomass," *Journal of Analytical and Applied Pyrolysis 6*, (1984), pp. 95–135.

Jandera et al., "Ion-Exchange Chromatography of Aldehydes, Ketones, Ethers, Alcohols, Polyols and Saccharides," *Journal of Chromotography*, 98 (1974) pp. 55–104.

Kang et al., "Ketene Formation From the Pyrolysis of Carbohydrates," research paper, Philip Morris Research Center, Richmond, Va., pp. 261–273.

Maga et al., "Pyrazine Composition of Wood Smoke as Influenced by Wood Source and Smoke Generation Variables," *Flavour and Fragrance Journal*, vol. 1, 37–42 (1985).

Martinsson et al., "Partition Chromatography of Sugars on Ion-Exchange Resins," *J. Chromotog.*, 50 (1970) pp. 429–433.

Menard et al., "Characterization of Pyrolytic Liquids from Different Wood Conversion Processes," Fifth Canadian Bioenergy R&D Seminar, undated, pp. 418–434.

Michelsen et al., "Spectroscopic Studies of Glycolaldehyde," *J. Mol. Structure*, 4 (1969) 293–302.

Namiki et al., "A New Mechanism of the Maillard Reaction Involving Sugar Fragmentation and Free Radical Formation," *New Mechanism of Maillard Reaction*, pp. 21–46.

Namiki et al., "Formation of Novel Free Radical Products in Early Stage of Maillard Reaction," *Prog. Fd. Nutr. Sci.*, vol. 5, pp. 81–91, 1981.

Pecina et al., "High-Performance Liquid Chromatographic Elution Behaviour of Alcohols, Aldehydes, Ketones, Organic Acids and Carbohydrates on a Strong Cation-Exchange Stationary Phase," *Journal of Chromatography*, 287 (1984) 245–258.

Piskorz et al., "On the Mechanism of the Rapid Pyrolysis of Cellulose," *Journal of Analytical and Applied Pyrolysis*, 9 (1986) 121–137.

Richards et al., "Influence of sodium chloride on volatile products formed by pyrolysis of cellulose: Identification of hydroxybenzens and 1-hydroxy-2-propanone as major products," Carbohydrate Research, 117 (1983) 322–327.

Roy et al., "The Pyrolysis under Vacuum of Aspen Poplar," paper published in Fundamentals of Thermochemical Biomass Conversion, Edited by R. P. Overend, (1985) pp. 237–256.

Samuelson et al., "Partition Chromatograph of Mixtures Containing Polyols and Carbonyl Compounds (Including Sugars) on Ion Exchange Resins," Acta Chem. Scand., 22 (1968) No. 4, pp. 1252–1258.

Scott et al., Chemicals and Fuels from Biomass Flash Pyrolysis, Renewable Energy Branch, Energy Mines and Resource Canada, Ottawa, Canada pp. 12–78 (1988).

Scott et al., "Sugars From Biomass Cellulose by a Thermal Conversion Process," paper published in Energy From Biomass and Wastes XIII Edited by Donald L. Klass, presented at conference in New Orleans Feb. 13–17, 1989, pp. 1349–1363.

Shafizadeh, "Industrial Pyrolysis of Cellulosic Materials," Applied *Polymer Symposium*, No. 28, 153–174 (1975).

Shafizadeh et al., "Pyrolysis of Cellulose," *Carbohydrate Research*, 29 (1973) 113–122.

Stassinopoulou et al., "A Study of the Dimeric Structures of Glycolaldehyde Solutions by NMR," *Tetrahedron.*, vol. 28, pp. 1257–1263 (1972).

Wodley, "Pyrolysis Products of Untreated and Flame Retardant-Treated α-Cellulose and Levoglucosan," Naval Radiological Defense Laboratory, pp. 835–851.

Pike et al., "Nutrition an Integrated Approach", 3rd Ed., John Wiley & Sons, N.Y., N.Y., p. 22 (1985).

Fennema ed., "Food Chemistry" 2nd Ed. Marcel-Dekker, Inc, N.Y. N.Y. pp. 98, 586 and 587 (1985).

FLAVORING AND BROWNING MATERIALS BY PYROLYSIS OF SUGARS AND STARCHES

CROSS REFERENCE TO RELATED APPLICATIONS

This application is a continuation-in-part of U.S. patent application Ser. No. 07/674,442, filed Mar. 27, 1991, now U.S. Pat. No. 5,292,541, which is a continuation-in part of Ser. No. 07/535,735, filed Jun. 8, 1990, now abandoned, Ser. No. 07/498,849, filed Mar. 26, 1990, now abandoned, Ser. No. 07/416,963, filed Oct. 4, 1989, now U.S. Pat. No. 5,039,537, and Ser. No. 07/358,650, filed May 26, 1989, now U.S. Pat. No. 4,994,297.

FIELD OF THE INVENTION

This invention relates to a process for producing browning liquid products and their use in coloring and flavoring foodstuffs. More particularly, this invention is directed to pyrolyzing sugars and starches to produce a browning liquid product for coloring and flavoring foodstuffs.

BACKGROUND OF THE INVENTION

Pyrolysis reactions produce a complex and variable reaction mixture including vaporous products which are liquid at room temperature. Pyrolysis is a general term for the thermal decomposition of any organic material (e.g., wood, plants, or fossil fuels) and can occur during a combustion process or in the absence of combustion. In the former, the oxidation of a portion of the organic material provides the heat required to vaporize and decompose the remainder. In the absence of combustion, heat is supplied indirectly from some other source (e.g., radiation, a solid or gaseous heat carrier or conduction through reactor walls).

Therefore, as used here and hereinafter, the term "pyrolysis" is defined as the thermal degradation of a material primarily into smaller, or simpler, molecules and into a minor portion of a residue, including ash and a residual polymeric material, or char. Similarly, here and hereinafter, the terms "pyrolysis product" and "pyrolysis liquid" are defined as the degradation products, or the smaller, simpler molecules, that result from pyrolysis, as opposed to the residue, including the pyrolytic char.

Therefore, pyrolysis of an organic material or biomass produces liquids (condensable vapors), gases (noncondensable vapors) and solids (char and ash), in varying proportions, depending upon reaction conditions. The term "pyrolysis product" is hereby further defined as the condensable vapors and noncondensable vapors resulting from pyrolysis. The term "pyrolysis liquid" is hereby further defined as the condensable vapors resulting from pyrolysis. The residue of char and ash is included neither in the definition of a pyrolysis product or a pyrolysis liquid. The pyrolysis liquid can be further subdivided into water-soluble condensable vapors and water-insoluble condensable vapors. The water-soluble condensable vapors are the desirable active ingredients for smoke flavoring.

Use of pyrolysis liquids, or solutions including pyrolysis liquids, as a replacement for smoking foodstuffs by direct contact with smoke produced from burning wood has become a standard industry practice. When applied to the surface of meats and other proteinaceous foodstuffs, conventional pyrolysis liquids (and solutions including pyrolysis liquids), termed "liquid smokes", not only give the foodstuff a characteristic smoke flavor, but react with the proteins to produce a coloring typical of smoked foodstuffs.

One such commercial liquid smoke product is the aqueous liquid smoke flavoring disclosed in Hollenbeck U.S. Pat. No. 3,106,473. This flavoring product is produced by slow pyrolysis or partial combustion of wood with limited access to air, followed by subsequent solvation of the desirable smoke constituents into water. The water-soluble condensable vapors are used for smoke flavor, while the water-insoluble condensable vapors which include tar, polymers, polycyclic aromatic hydrocarbons (including benzo(a)pyrene), waxes and other compounds unsuitable or undesirable for use in food applications are discarded.

Another method of producing a pyrolysis liquid for smoke flavoring foods is the fast pyrolysis of wood or cellulose disclosed in Underwood et al. in U.S. Pat. No. 4,876,108. The pyrolysis liquids produced by the fast pyrolysis process are collected and diluted with water to achieve a partial phase separation and to provide an aqueous liquid smoke-flavored solution.

Regardless of whether wood or cellulose is pyrolyzed by a slow pyrolysis method or by a fast pyrolysis method, the resulting smoke-flavored pyrolysis liquid, or a solution including the pyrolysis liquid, imparts a stronger than desirable smoke flavoring to some foodstuffs for a given degree of smoke coloring for the tastes of some consumers. Even though such consumers prefer a very mild to little smoke flavor, these consumers still prefer a flavored foodstuff, especially meat, having the typical full-brown color associated with well-smoked foodstuffs. Even though a need exists for such a mild, smoke-flavored pyrolysis liquid, or solution including such a pyrolysis liquid, apparently none is presently available.

SUMMARY OF THE INVENTION

The present invention provides a high browning, aqueous composition derived from a sugar or a starch, or a mixture thereof, wherein the composition has a soluble organic content of less than about 50° Brix, a browning index greater than about 30 and a ratio of titratable acidity to browning index of less than about 0.06. Preferably, the high browning, aqueous composition has a browning index greater than about 50 and more preferably greater than about 75. A preferred high browning, aqueous composition is a liquid product derived from corn syrup, wherein the high browning, aqueous composition has a soluble organic content of about 45° Brix, a browning index of about 104 and a titratable acidity of about 3.2%.

The reduced acidity and high browning index of the a high browning, aqueous composition make the composition particularly useful in coloring encased foodstuffs, such as sausages or other meat products are prepared by known casing processes.

The present invention also provides a method of producing a high-browning liquid product comprising the steps of: pyrolyzing a feedstock selected from the group consisting of a sugar, a starch and mixtures thereof to produce a vaporous pyrolysis product including condensable vapors and noncondensable vapors; separating the vaporous pyrolysis product from the feedstock and pyrolytic residue; and condensing the condensable vapors in the vaporous pyrolysis product to produce a water-soluble pyrolysis liquid having little or substantially no detectable smoke flavoring ability when evaluated by taste.

Preferably, sufficient water is added to the water-soluble pyrolysis liquid to dilute the water-soluble pyrolysis liquid and thereby reduce the Brix value to about 30° Brix or lower. Diluting the water-soluble pyrolysis liquid with water ensures complete separation of the undesirable water-insoluble components from the desirable water-soluble components of the water-soluble pyrolysis liquid. Specifically, if the Brix value of the water-soluble pyrolysis liquid is greater than about 30° Brix, the separation of benzo(a)pyrene from the water-soluble pyrolysis liquid may be incomplete.

Furthermore, it also is preferred that the water-soluble pyrolysis liquid phase is diluted to less than about 42° Brix when further extracting or otherwise treating the water-soluble pyrolysis liquid. At Brix values greater than about 42° Brix, subsequent extraction or treatment steps can be less effective primarily due to the greater solvating effects of the organic components in more concentrated aqueous solutions.

The resulting water-soluble pyrolysis liquid is capable of imparting a full brown color to a foodstuff, such as meat and specifically bacon or sausage, when a sufficient amount of the water-soluble pyrolysis liquid is applied to the foodstuff, followed by heating to complete processing of the treated foodstuff. A foodstuff is not browned by simply contacting the foodstuff with the water-soluble pyrolysis liquid, heating or cooking is required to brown the foodstuff. Furthermore, treatment of a foodstuff with the water-soluble pyrolysis liquid, followed by heating, provides a brown-colored foodstuff having little or substantially no smoke flavor or aroma.

The water-soluble pyrolysis liquid described above, preferably having a maximum Brix value of about 30°, can be subjected to additional process steps to further lower the amount of flavoring materials in the product. In one embodiment, the water-soluble pyrolysis liquid is extracted with a suitable water-insoluble organic extraction solvent, such as methylene chloride or chloroform, to remove flavoring materials, and especially food flavoring materials which provide smoke flavor and aroma, without removing those materials which provide browning activity, like hydroxyacetaldehyde. Hydroxyacetaldehyde is water soluble, but is quite insoluble or only very slightly soluble in nonpolar organic solvents, such as methylene chloride.

Preferably, the water-insoluble organic solvent has a water solubility of 3 parts or less per 100 parts of water, by volume. Generally, suitable organic extraction solvents have a proper range of hydrogen bonding parameters and an appropriate polarity index to solubilize the undesirable flavor-supplying organic materials present in the water-soluble pyrolysis liquid. Exemplary, but non-limiting, solvents include methylene chloride, chloroform, carbon tetrachloride, 1,1,1-trichloroethane, ethylene dichloride and mixtures thereof.

After extraction, the organic extraction solvent then is separated from the aqueous water-soluble pyrolysis liquid to yield an extracted browning liquid product which has substantially no detectable flavoring ability when evaluated by taste. Preferably, the water-insoluble organic extraction solvent has a sufficiently low vapor pressure for easy removal of solvent residues from the water-soluble pyrolysis liquid.

The water-soluble pyrolysis liquid, whether or not extracted with a suitable organic extraction solvent, also can be treated with a nonionic resin, a cationic resin or a combination thereof, to remove contaminants and undesirable flavoring materials from the water-soluble pyrolysis liquid. The resin treatment of liquid solutions produced by slow pyrolysis of wood is described in U.S. Pat. No. 4,959,232, incorporated herein by reference. The conditions disclosed therein are suitable for processing a water-soluble pyrolysis liquid derived from a sugar, starch or mixtures thereof, with or without a prior organic solvent extraction. The resulting resin-treated, browning liquid product has substantially no detectable flavoring ability when evaluated by taste.

The browning liquid product resulting from the extraction and/or resin treatment of a water-soluble pyrolysis liquid either can be diluted with water or can be concentrated for an appropriate food browning ability which depends on the method of applying the water-soluble pyrolysis liquid and the type of foodstuff to be treated.

DETAILED DESCRIPTION OF THE INVENTION

The present invention provides a method of producing useful flavoring and browning products by pyrolyzing sugars, starches or mixtures thereof. The sugar or starch can be pyrolyzed by slow pyrolysis, although fast pyrolysis is preferred.

Slow pyrolysis is characterized by relatively slow thermal reactions occurring at moderate temperatures. A typical slow pyrolysis reactor temperature is approximately 420° C. Depending on the method of heating, the temperature gradient in a slow pyrolysis reactor can be from 600° C. at the heat transfer surface to 250° C. at the feedstock surface. Residence times of the solids in the slow pyrolysis reactor may be about one to ten minutes.

The fast pyrolysis process is designed to achieve a very high temperature in a minimum amount of time, as well as having a relatively short reactor residence time at the sugar or starch pyrolysis temperature. Short residence times at high temperatures can be achieved in several ways. However, the parameters to be optimized in any fast pyrolysis of a sugar or starch to produce a suitable liquid product in high liquid yields include:

1) High heating rates of the sugar or starch feedstock (greater than 1,000° C. per second (sec));

2) Vapor residence times (i.e., the average time that the gas/vapor phase remains in the reactor) greater than about 0.05 sec and less than about 1.0 sec and preferably less than 0.6 sec;

3) Isothermal reaction temperatures between about 400° C. and about 800° C.; and 4) Quenching of the liquid/vapor product to temperatures of less than 300° C. in less than 0.6 sec.

One fast pyrolysis method, a vacuum pyrolysis method, is based on the principle that primary pyrolysis products can be withdrawn from the reactor under vacuum conditions before they have a chance to react further and produce secondary pyrolysis products. This vacuum pyrolysis method has been described by Roy et al. in "Pyrolysis Under Vacuum of Aspen Poplar" *Fundamentals of Thermo-Chemical Biomass Conversion,* R. P. Overend et al. (editors), Elsevier (publisher) (1985), incorporated herein by reference. In this process, the solid sugar or starch feedstock remains in the reactor until completely reacted and the heating rate of the sugar or starch is much slower than a rapid thermal process or a fluidized bed pyrolysis process, both subsequently described hereinafter. Reactions of primary pyrolysis products to produce secondary pyrolysis products, however, are reduced by quickly removing and cooling the primary pyrolysis vapors. Accordingly, the heating rate is less significant because secondary reactions are limited.

Another fast pyrolysis method, often referred to as flash pyrolysis, uses a fluidized bed reactor system operating at a high temperature, generally between about 400° C. and 650° C. Reactor residence times of about 0.5 to about 3 seconds are particularly suitable. (See, e.g., Scott et al. "Production of Liquids from Biomass by Continuous Fast Pyrolysis," *Bioenergy* 84 Vol. 3, *Biomass Conversion* (1984), incorporated herein by reference).

A third fast pyrolysis method, referred to as rapid thermal processing, is a fast pyrolysis method which uses hot particulate solids and/or inert gases to rapidly transfer heat to a feedstock in a reactor system. These fast pyrolysis methods offer much improved yields and improved quality of liquid products compared to slow, low temperature pyrolysis systems.

A variety of sugar or starch feedstocks can be pyrolyzed. A solid sugar or starch, as well as solutions, syrups or suspensions of a sugar or starch in a solvent or liquid carrier, can be pyrolyzed. Preferably, a specific feedstock is selected to allow use of feed systems or injectors that are compatible with specific pyrolysis apparatus and equipment. Furthermore, it is not necessary for the feedstock to be homogenous. Mixtures of impure sugar or starch compositions can be used as pyrolysis feedstocks provided the additional components or impurities do not interfere with either pyrolysis of the feedstock or isolation of the water-soluble pyrolysis liquid, or adversely affect the pyrolysis apparatus.

Some of the sugars which can be pyrolyzed according to the present invention are mono-, di- and trisaccharides. Specific sugars and sugary products which can be pyrolyzed are glucose, sucrose, dextrose, invert sugar, galactose, lactose, corn syrup, malt syrup and molasses. Specifically, cow's milk is a well known source of lactose. Lactose is also present in whey, a relatively abundant by-product of the cheese making process. Specifically, low nitrogen content whey solutions containing lactose, as well as other by-products of the cheese making process, can be pyrolyzed. Thus, lactose is a unique, readily-available sugar that is not derived from plant sources. Due to availability and cost, dextrose, lactose and corn syrups are preferred sugars for use in the present invention.

Starches which can be pyrolyzed include corn starch, potato starch, wheat starch, oat starch, tapioca starch and rice starch.

Therefore, a wide variety of sugars can be thermally degraded, i.e., pyrolyzed, to form a water-soluble pyrolysis liquid containing the food browning agent hydroxyacetaldehyde (HAA). The water-soluble pyrolysis liquid is essentially free of pyrolytic residue, such as ash and pyrolytic char. The water-soluble pyrolysis liquid therefore does not brown a foodstuff by dying or staining the foodstuff, but by reacting with proteins present in the foodstuff during cooking or heating. For example, each sugar listed in Table 1 was added to water, individually, to make a 5% wt/vol sugar solution. Each solution then was injected individually into a Varian Gas Chromatograph having an injection port temperature of 250° C. to give pyrolyzed products, including HAA. The amount of HAA produced by each listed sugar is set forth in Table 1.

TABLE 1

| SUGAR | NUMBER OF CARBON ATOMS | PARTS PER MILLION OF HAA FORMED |
|---|---|---|
| Glyceraldehyde | 3 | 6366 |
| Threose | 4 | 9784 |
| Erythrose | 4 | 12303 |
| Ribose | 5 | 3632 |
| Arabinose | 5 | 2000 |
| Xylose | 5 | 4266 |
| Lyxose | 5 | 18895 |
| Allose | 6 | 1000 |
| Altrose | 6 | 500 |
| Glucose | 6 | 900 |
| Mannose | 6 | <10 |
| Gulose | 6 | 2994 |
| Idose | 6 | 5318 |
| Galactose | 6 | <10 |
| Talose | 6 | 1829 |
| Sorbose | 6 | 3447 |
| Fructose | 6 | 1959 |
| Cellobiose | 12 | <10 |
| Lactose | 12 | <10 |
| Maltose | 12 | <10 |
| Sucrose | 12 | <10 |

While varying amounts of HAA were produced from each of the above-identified sugars, the results listed in Table 1 demonstrate that the observed yield of HAA is related to the thermal lability of the sugar. Due to the 250° C. injector port temperature limit in this experiment, only lyxose approached the theoretical maximum yield of two divided by the number of carbon atoms per monosaccharide unit, the lyxose yield being 38%. It can be concluded that nearly all simple sugars can be pyrolyzed to yield varying amounts of HAA at about 250° C.

Both aldoses and ketoses (fructose and sorbose are ketoses, the remaining sugars are aldoses) pyrolyze to yield HAA. Galactose and mannose are more thermally resistant to pyrolysis to HAA than the other sugars. Neither galactose nor mannose could be pyrolyzed under the conditions of this experiment at 250° C. Furthermore, additional thermal stability results from combining two or more simple sugars in a pyrolyzed molecule, as seen in Table 1 from the data for cellobiose, lactose, maltose and sucrose.

Based on the data for glucose and galactose when pyrolyzed independently, it was expected that, on a molar basis, the yield of HAA, a known food browning agent, from lactose would be about half the yield from glucose. Surprisingly, HAA is formed from the galactose portion of lactose as well as from the glucose portion. Either the epidermic alpha- or beta-form of lactose is suitable as the yield is independent of the type of disaccharide linkage.

While not meant to be a limitation of the mechanism of carbohydrate pyrolysis, it is theorized that a kinetic bias to cleave lactose between carbons 2 and 3 to yield the two carbon HAA exists. A mechanism which suggests this bias is reported by Piskorz et al. *J. Anal. Appl. Pyrol.*, 9:121–137 (1986). The observed yield of the pyrolysis products is believed to be a matter of having sufficiently rapid heat transfer for the kinetics of pyrolysis to favor this pathway as opposed to dehydration by other alternate pathways. Short vapor residence times are believed to limit undesired secondary reactions. Furthermore, no oxygen should be present.

The desired water-soluble pyrolysis liquids of this invention can be applied directly to a foodstuff using techniques and methods well known in the liquid smoke art. Application techniques such as dipping, spraying, pumping and soaking are all suitable methods for applying a high browning aqueous composition of the present invention to a foodstuff. Mere application of the water-soluble pyrolysis liquid to a foodstuff does not brown the foodstuff. Therefore, unlike a conventional caramel product, the water-soluble pyrolysis product is not a dye or a stain.

The browning liquid product of this invention provides the capability of browning a foodstuff with a minimum concentration of HAA in the browning liquid product. Sufficient concentrations of HAA in an aqueous solution required to impart a rich golden brown color to meat cooked in a microwave oven are listed in Table 2. To impart color, an aqueous solution of the browning liquid product was applied to the surface of Swift Premium Brown and Serve Sausages by a 2 to 3 second dip. Cooking or heating is necessary for the browning liquid product to color the sausages. Therefore, the sausages were microwaved for one minute, along with untreated sausages which serve as controls. After microwaving, the sausages were evaluated for visual color appeal. Thus, browning liquid products having an HAA concentration as low as 0.05% wt/vol can be used to impart a noticeable golden brown color to cooked sausages.

TABLE 2

| HAA in Solution (% Wt/vol) | Surface Coating Concentration (µg HAA/cm2) | Total Product Loading (µg HAA/g product) | Color Description |
| --- | --- | --- | --- |
| 2.0 | 184 | 350 | Very Brown |
| 1.0 | 92 | 175 | Very Brown |
| 0.5 | 46 | 88 | Golden Brown |
| 0.1 | 9 | 18 | Light Golden Brown |
| 0.05 | 5 | 9 | Very Light Brown |
| 0 | 0 | 0 | Grayish White |

HAA = hydroxyacetaldehyde

In addition to direct application to a foodstuff, a browning liquid product of this invention also can be applied indirectly to foodstuffs by applying the browning liquid product to sausage and food product casings. The application to casings indirectly allows a processor to impart a brown color to a particular food product.

Any well-known method can be used to contact the sausage or foodstuff casing with the browning liquid product. See, for example, the methods disclosed in U.S. Pat. Nos. 3,330,669 and 4,504,500. Suitable methods for contacting foodstuff casings with the browning liquid product are also described in U.S. Pat. No. 5,039,537, incorporated herein by reference.

Food casings suitable for treatment with a browning liquid product of the present invention include tubular casings, and preferably tubular cellulosic casings, that are prepared by any of the methods well known in the art. Such casings are generally non-fibrous, flexible, thin-walled seamless casings formed of regenerated cellulose or cellulose ethers, such as hydroxyethyl cellulose, in a variety of diameters. Also suitable are tubular cellulosic casings having a fibrous reinforcing web embedded in the wall of the casings, and commonly called fibrous food casings.

The browning liquid product can be applied to the outer surface of the food casing by passing the casing through a bath of the browning liquid product. The browning liquid product generally is allowed to soak into the casing for a sufficient time to incorporate the desired amount of browning liquid product into the casing before doctoring off any excess liquid product by passing the casing through squeeze rolls or wipers. The browning liquid product also can be applied to the casing externally by methods other than dipping, such as by spraying, brushing or roll-coating.

Another method of treating the casing with a browning liquid product of this invention involves passing a flattened, tubular, cellulose sausage casing over guide rolls through a dip tank which contains the browning liquid product. The casing passes over additional guide rolls after exiting the dip tank, and then passes between squeeze rolls which minimize any excess carryover of the browning liquid product. The total contact time between the casing and the browning liquid product in the dip tank, with excess browning liquid product on the casing passing over the guide rolls before the casing passes through the squeeze rolls, typically determines the amount of coloring and flavoring casing incorporated into the casing from the browning liquid composition. The casing then proceeds through further conventional further processing steps, including humidification, as may be required, and shirring.

Alternatively, the browning liquid product can be applied to the internal surface of the casing by any of several well-known procedures. These include slugging or bubble coating, spraying, and coating while shirring. The slugging method for coating the inside of a casing involves filling a portion of the casing with the browning liquid product, so that the slug or coating material generally resides at the bottom of a "U" shape formed by the casing, and then moving the continuous indefinite length of casing so that the slug of browning liquid product remains confined within the casing, while the casing moves past the slug and is coated on its inside wall by the browning liquid product contained within the slug.

The casing then can be shirred by conventional methods or, prior to shirring, can be dried or humidified before shirring to a water content suitable for shirring or further processing. The need for conventional drying or humidification after the external liquid treatment depends on the water content of the casing after treatment and the type of casing. If the casing is a non-fibrous casing, a water content within the range of about 8–18 wt. % water immediately before shirring is typical, and for fibrous casing a water content within the range of about 11–35 wt. % water immediately before shirring is typical, where weight percent is based on the total weight of casing including water.

The HAA present in the browning liquid product is a particularly preferred component when treating collagen casings because the difunctional HAA is an effective crosslinking agent. Thus, the physical properties of the collagen casings can be improved by the crosslinking provided by HAA.

In the indirect application of the browning liquid product to sausage or food casings, the lack of a strong or an undesirable flavor is a notable, additional advantage. Conventional liquid smoke products derived from wood or cellulose generally are applied to a casing at high concentrations to impart sufficient color or browning to the encased foodstuff. These high concentrations, however, typically impart a smoke flavor which is sometimes more intense than desired by consumers. The use of a present browning liquid product on foodstuff casings allows a processor to achieve the desired brown color while imparting substantially no detectable smoke flavoring to the foodstuff when evaluated by taste. In addition, if a water-soluble pyrolysis liquid, which has been neither extracted with an organic extraction solvent nor treated with an ion exchange resin, is applied to a foodstuff casing, the foodstuff can be sufficiently browned and the foodstuff has little to substantially no detectable smoke flavoring when evaluated by taste.

BRIEF DESCRIPTION OF THE DRAWINGS

Details of embodiments of the invention are described by reference to the accompanying drawings in which.

DETAILED DESCRIPTION OF THE DRAWINGS

In the following description the corresponding elements as shown in each figure of the drawings are given the same reference number.

Figure 1:
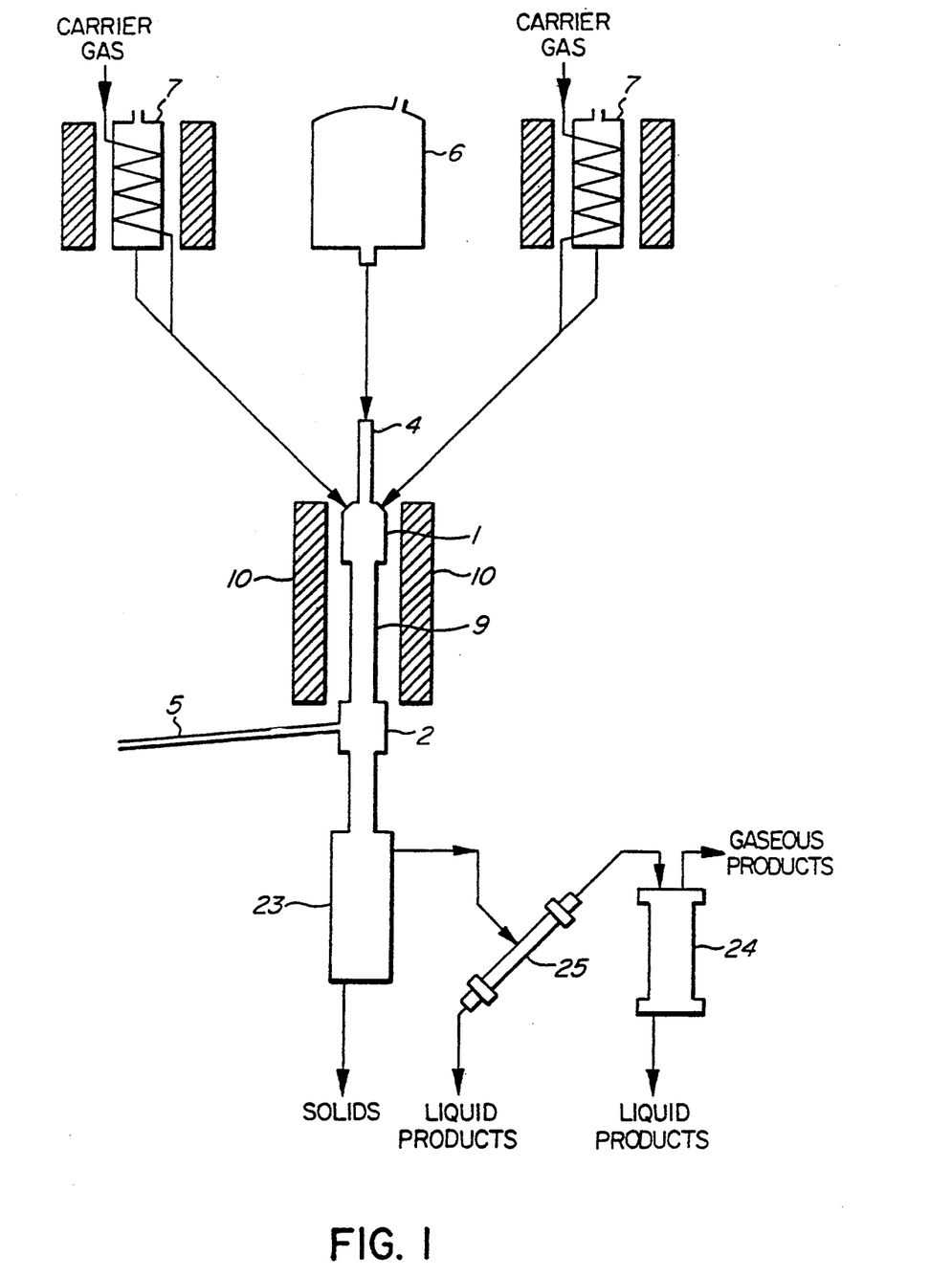
FIG. 1 is a schematic representation of an apparatus useful in a fast pyrolysis method referred to as rapid thermal processing.
Figure 2:
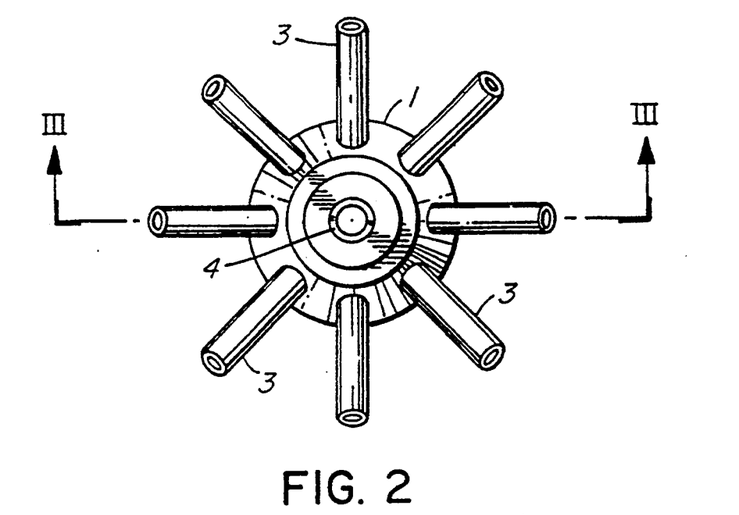
FIG. 2 is a top plan view of the reactor of the pyrolysis apparatus of FIG. 1.
Figure 3:
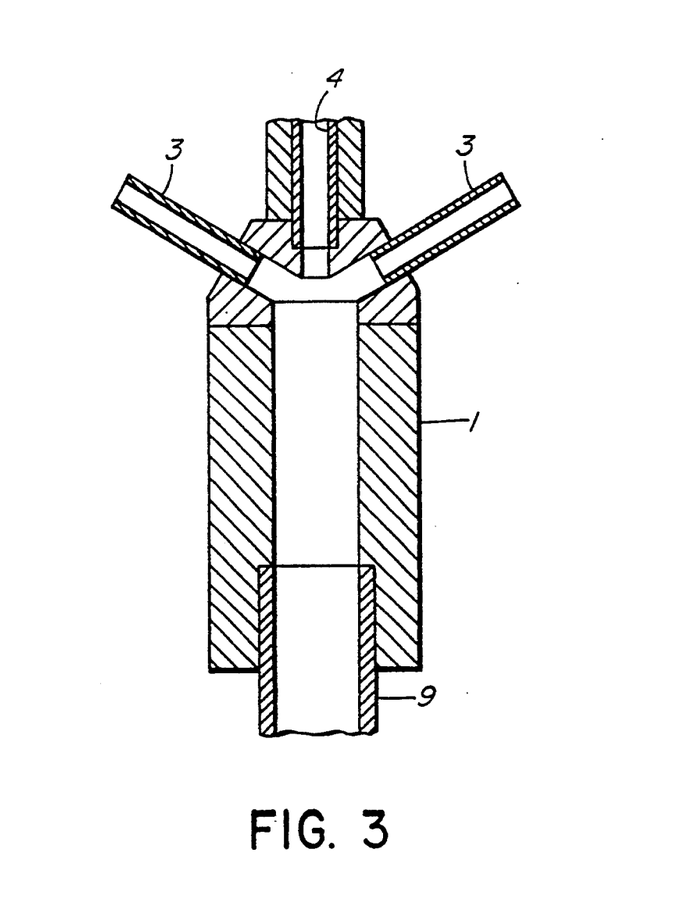
FIG. 3 is a sectional view taken on the line III—III of FIG. 2.

While FIGS. 1 to 3 of the accompanying drawings and the description thereof pertain to rapid thermal processing, similar products can be produced using other fast pyrolysis apparatus and processes, including vacuum pyrolysis and flash pyrolysis, as well as other systems that result in a high temperature with a limited residence time.

The major components of the apparatus used in the rapid thermal process are illustrated in FIG. 1. Rapid mixing and heat transfer are carried out in two vessels. The first vessel, or thermal mixer 1, allows heat to be transferred to the sugar or starch feedstock from hot inert particulate solids, an inert gas which can be gaseous nitrogen, or a combination of the two. The second vessel, or quencher 2, allows fast quenching of the reaction products to prevent the initial pyrolysis products from undergoing secondary reactions.

As shown in FIGS. 2 and 3, thermal mixer 1 has opposing converging inlets 3 for the heated inert particulate solids. This system effectively destroys the radial momentum of the particulate heat carrier causing severe turbulence. The particulate feedstock (or atomized sugar or starch liquid) then is injected from the top of thermal mixer 1 through a cooled tube 4 into the turbulent region where mixing occurs within 30 milliseconds.

After heating and mixing occur, the feedstock and the primary pyrolysis vapors are maintained at the reaction temperature for between 0.03 and 2 seconds. The primary pyrolysis vapors are produced as soon as the feedstock is sufficiently heated to start the pyrolysis reactions. The hot gaseous product is rapidly cooled (i.e., less than 30 milliseconds) by the injection of a single tangential stream of cryogenic nitrogen.

Mechanical table feeders can be used to supply a particulate feedstock to the reactor system. The feedstock passes from a sealed hopper 6 through a double funnel system and is thereby metered onto a rotating table (not shown). Two fixed armatures sit near the surface of the rotating table and plough the particulate feedstock off the outer circumference. The particulate feedstock then falls from the rotating table into a conical chamber (not shown) where the feedstock is picked up and carried into the transport line by nitrogen gas. The feed rate of the sugar or starch particulate feedstock is controlled by setting the gap between the lower funnel and the table. Fine control is exercised by the rotation speed of the table.

When inert particulate solids are used to supply the process heat, feeders 7 direct the hot inert particulate solids through a non-mechanical high temperature valve (not shown) which operates at the reaction temperature. These hot inert particulate solids are then directed to the thermal mixer 1.

The solid particulate feedstock (or atomized sugar or starch liquid) then is injected into thermal mixer 1 through a water-cooled or air-cooled tube 4 into the turbulent region of thermal mixer 1 where effective mixing and rapid heating to at least 400° C. occurs within 0.10 second, and preferably within 0.03 second.

Fast pyrolysis of the sugar or starch feedstock initiated in thermal mixer 1 continues in a transport reactor 9. Transport reactor 9 is a conduit which is heated by an electrical oven 10 or heated by the combustion of natural gas or propane. The mixture of hot gases and feedstock passes from thermal mixer 1 through transport reactor 9 to quencher 2 and to a solids separator 23. By varying the reactor volume and by manipulating the inert heat carrier/feedstock flow rates, the residence time of the feedstock and pyrolysis products in thermal mixer 1 and transport reactor 9 can be varied between 30 msec (milliseconds) and 3 sec. Reactor temperatures can be in the range of about 400° C. to about 1000° C. Preferably, reactor temperatures are about 400° C. to about 800° C., and more preferably about 500° C. to about 600° C. The heating rate that can be achieved with this apparatus is over 10,000° C. per second.

A cyclonic condensor 25 can be used to increase the yield of recovered pyrolysis liquid. In addition, an electrostatic precipitator 24 can be integrated into a downstream gas line to recover additional pyrolysis liquid. The noncondensable vapors generated by the pyrolysis reaction are vented. -The residual solids generated by the pyrolysis reaction (i.e., char and ash) are discarded.

After collection of the pyrolysis liquid, water is added to the pyrolysis liquid to cause phase separation and thereby reduce benzo(a)pyrene and tar concentration in the pyrolysis liquid. The amount of water added beyond the amount necessary to achieve effective phase separation is to some extent a matter of choice. However, it is generally desirable to dilute the raw pyrolysis liquid with sufficient water to produce a water-soluble pyrolysis liquid having a maximum specific gravity not significantly greater than 30° Brix.

Figure 4:
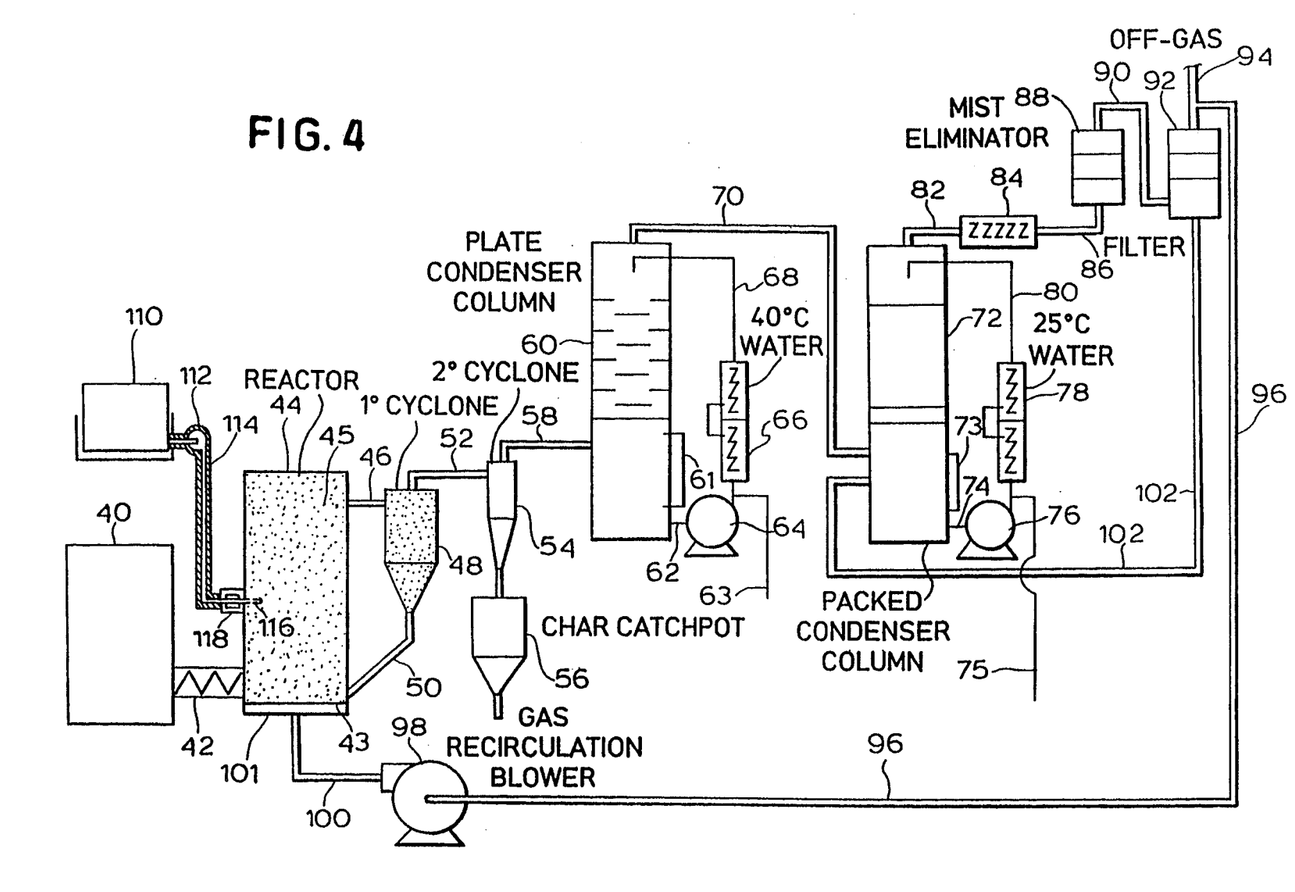
FIG. 4 is a schematic representation of a fast pyrolysis apparatus including an upflow reactor.

FIG. 4 illustrates another apparatus useful for the fast pyrolysis of sugars and starches by the rapid thermal process. Bin 40 stores a supply of a feedstock solid sugar or starch in granular or powder form. The feedstock is fed from bin 40 to the lower interior portion of a reactor 44 above a windbox 101 and a grid plate 43 by an auger 42. Auger 42 can be water cooled at the inlet to reactor 44 to prevent premature pyrolysis of the feedstock, which can produce tarry materials.

Alternatively, a solution or syrup of a carbohydrate-containing liquid feedstock can be injected into reactor 44 using any suitable well known injector apparatus.

Heated storage tank 110 stores a supply of a liquid feedstock. The liquid feedstock is pumped from storage tank 110 by a pump 112 through a clean jacketed conduit 114. The liquid feedstock enters reactor 44 through an injector nozzle 116. Injected nozzle 116 can be cooled at an inlet in reactor 44 by a water-cooled jacket 118 to prevent premature pyrolysis of the liquid feedstock in the injector nozzle.

A stream of recirculation gas transport fluid is fed by a conduit 100 into windbox 101, through grid plate 43 and into the lower portion of reactor 44 containing a heat transfer medium 45, such as sand. Rapid mixing and conductive heat transfer from heat transfer medium 45 to the sugar or starch feedstock occurs in reactor 44. Pyrolytic conversion of the feedstock to a raw product vapor is initiated and continues through reactor 44 with upward flow into a primary cyclone separator 48. The pyrolysis stream comprising heat transfer medium 45 and pyrolysis vapor is directed from reactor 44 through a conduit 46 and is fed and is to primary cyclone separator 48. The hot heat transfer medium 45 is removed from the stream of raw product vapor in primary cyclone separator 48 and recycled by means of a conduit 50 to reactor 44. Recycled heat transfer medium 45 is reintroduced into the interior lower portion of reactor 44 at a point above grid plate 43. Raw product vapor containing char is directed from primary cyclone separator 48 by a conduit 52 and is fed to a secondary cyclone separator 54, such as a high efficiency reverse flow cyclone separator. Char and solid sand fines are removed in secondary cyclone separator 54 and fed therefrom to a char catchpot 56 for disposal or further handling as desired.

The resulting hot stream of vaporous pyrolysis product is directed through the top of secondary cyclone separator 54 through a conduit 58 which feeds the vaporous pyrolysis product comprising condensable and noncondensable vapors, and some fine residual char and ash, to the lower interior space of a baffled first condenser 60 where the vaporous pyrolysis product is immediately quenched. First condensor 60 uses the pyrolysis liquid as the quench medium.

The condensed pyrolysis liquid is withdrawn from the bottom of first condensor 60 through a conduit 62 and is fed to a pump 64 which pumps the condensed pyrolysis liquid to a heat exchanger 66 indirectly cooled by water. The cooled pyrolysis liquid is directed from heat exchanger 66 through a conduit 68 and is returned to the top of first condenser 60 as a spray. A conventional transparent vertical sight indicator 61 is mounted on the lower portion of first condenser 60. The sight indicator has high and low liquid level marks. When the volume of pyrolysis liquid in first condenser 60 reaches the high level mark, pyrolysis liquid is withdrawn through a conduit 63 until the liquid level in first condenser 60 reaches the low level mark of sight indicator 61. Pyrolysis liquid then is accumulated in condenser 60 until the pyrolysis liquid again reaches the high level mark of sight indicator 61, when the pyrolysis liquid withdrawal step is repeated.

Noncondensed vapor of the pyrolysis product is directed through the top of condenser 60 through a conduit 70 and is fed to a packed second condenser column 72 where the noncondensed vapor is further cooled. Condensed pyrolysis liquid is withdrawn through a conduit 74 from the bottom of second condenser column 72 and is fed to a pump 76 which pumps the condensed pyrolysis liquid through a water-cooled heat exchanger 78. Cooled pyrolysis liquid is directed from heat exchanger 78 through a conduit 80 and is fed to the top of second condenser column 72. A second conventional transparent vertical sight indicator 73 is mounted on the lower portion of second condenser column 72. Second sight indicator 73 has high and low liquid level marks. When the high level mark of second sight indicator 73 is reached, pyrolysis liquid is withdrawn from second condenser column 72 through a conduit 74 until the liquid level reaches the low level mark of second sight indicator 73.

A remaining vapor stream is directed from the top of packed second condenser column 72 through a conduit 82 and a is fed through a water cooled heat exchanger 84 and a conduit 86 which feeds the remaining vapor stream to a mist eliminator 88. The remaining vapor stream is directed from mist eliminator 88 through a conduit 90 which delivers the remaining vapor stream to a filter 92. Any condensed liquid is removed from the bottom of filter 92 by means of a conduit 102, and the liquid is recirculated to the bottom portion of second condenser column 72 above the level of pyrolysis liquid in second condenser column 72. A portion of the resulting, clean noncondensable pyrolysis gas stream is vented from filter 92 by a conduit 94 to waste, while a second portion is directed from conduit 94 and fed to a conduit which feeds the noncondensable pyrolysis gases to a gas recirculation blower 98. The recirculated, noncondensable gas is fed from blower 98 to conduit 100 which feeds the noncondensable gas into the bottom of reactor 44.

The following examples are presented to further illustrate the invention. In the examples, the concentration values for the organic components in the described liquids are given as ° Brix values. The ° Brix values were obtained using standard refractory techniques which are well known in the sugar industry. The percent weight per volume (% wt/vol) values for HAA were obtained using gas chromatography and comparing the peak integrations of a sample of a liquid (diluted if necessary) with peak integrations of a standard curve generated from a 1–5% serial dilution of HAA in water. Gas chromatograms were run on a Varian Gas Chromatograph (Model 3300 equipped with a Varian Integrater Model 4290) fitted with a fused-silica capillary column (either a 0.25 mm × 60 m J&W DB1701 column or a 0.25 mm × 30 m J&W DB-Wax column) using hydrogen carrier gas at a flow rate of 2.0 ml/mm and a temperature program of 40° C. initial temperature, zero minute hold followed by increasing the temperature at 8.0° C./minute to 255° C. The injector temperature was 220° C., the detector temperature was 300° C.

Under these conditions, the retention time of HAA in the J&W DB-1701 column was 2.85 minutes and on the J&W DB-Wax column was 4.70 minutes.

EXAMPLE 1

Dextrose (Cerelose® dextrose 2001, D.E. 95, Corn Products, Inglewood Cliffs, N.J.) was fast pyrolyzed at about 550° C. using an apparatus as illustrated in FIG. 4 with a vapor residence time of 0.7 seconds at a pressure of 1–1.5 psi. The pyrolysis product, i.e., condensable and noncondensable gases, was condensed by direct contact with 20° C. recirculating water to provide a pyrolysis liquid. Above five pounds of dextrose were fed to the apparatus over a twenty minute period.

The resulting pyrolysis liquid had a Brix value of about 4° and contained about 0.5% wt/vol HAA. The pyrolysis liquid then was concentrated at 50° C. under a water aspirator vacuum of about −28.5 inches of mercury to remove excess water to give a concentrated pyrolysis liquid of about 63° Brix and an HAA concentration of about 29% wt/vol.

EXAMPLE 2

Powdered dextrose was pyrolyzed in a downflow transport reactor (FIG. 1) using sand as the heat transfer media. The reactor temperature was 600° C. and the vapor residence time in the reactor was 75 msec. The pyrolysis liquid yield was 83.5%, noncondensable gases yield was 14% and char yield was 2.5%. The composition of the condensed raw pyrolysis liquid was as follows:

| | |
|---|---|
| Brix | 64.7° |
| Water | 34.3% |
| Hydroxyacetaldehyde | 25.5% |
| Acetol | 2.6% |
| Acetic acid | 1.6% |
| Other organics (including hydroxymethyl furfural) | 36.0% |

EXAMPLE 3

The initial 4° Brix pyrolysis liquid obtained in Example 1 was concentrated by evaporation under reduced pressure to give a 18° Brix solution containing about 5% wt/vol HAA. A portion of this pyrolysis liquid (60 ml) was extracted with three individual portions of food grade methylene chloride (20 ml) to remove flavor components. The extracted pyrolysis liquid then was treated batchwise with two types of food grade resins, first with Rohm & Haas nonionic resin XAD-4 (6 g) and then with Rohm & Haas cationic resin IR-120 (3 g) to remove additional flavor constituents. The resulting extracted pyrolysis liquid (about 12.9° Brix) was evaporated to remove low molecular weight volatile components and residual methylene chloride. The concentrated extracted pyrolysis liquid was about 50° Brix and contained about 32% wt/vol HAA. Subsequently, the concentrated extracted pyrolysis liquid was diluted with water to a concentration of 13° Brix, which is a suitable concentration for direct application to a foodstuff.

The 13° Brix browning composition, containing about 5% wt/vol HAA, was applied to the surface of Swift Premium Brown and Serve Sausages (Swift-Eckrich, Inc., Oak Brook, Ill.). The treated sausages and untreated sausages (which were used as a control) were microwaved. Prior to microwaving, the treated and untreated sausages were not distinguishable by visual inspection. After microwaving, sausages treated with the 13° Brix browning composition had a rich golden brown color compared to the untreated control sausages which had a grayish white color. There was no palatable difference in terms of flavor between the two groups of sausages. This shows that the flavorless browning composition browned the sausages without also contributing a detectable flavor to the sausages.

EXAMPLE 4

This example describes a method for producing a high browning, flavorless aqueous composition from dextrose and its usefulness in browning foods in a microwave oven.

Dextrose was fast pyrolyzed at about 550° C. in an upflow circulating fluidized bed reactor as illustrated in FIG. 4. The vapor residence time was about 0.7 second, the pressure was about 1-1.5 psi and the pyrolysis product was condensed and solubilized by direct contact with circulating 20° C. water. The resulting aqueous pyrolysis liquid contained about 4° Brix total organic solids as determined by refractive index, and about 0.5% wt/vol HAA as determined by gas chromatography. This pyrolysis liquid then was concentrated to 18° Brix organic solids by rotary evaporation and was found to contain about 6% wt/vol HAA. A portion of this pyrolysis liquid (60 ml) then was extracted with three individual portions of food grade methylene chloride (20 ml) to remove flavor components. The resulting extracted pyrolysis liquid then was concentrated to 50° Brix organic solids to remove low molecular weight flavor components. The resulting extracted pyrolysis liquid contained 23% wt/vol HAA by gas chromatography. Gas chromatography analysis also showed that furfural, phenolics, and pyrazines were the major flavor components removed by the extraction and evaporation. Water then was added to dilute the extracted pyrolysis liquid back to 5% wt/vol HAA. The organic solids content of the resulting diluted extracted pyrolysis product was 12° Brix.

This diluted, flavorless foodstuff browning composition was applied to the surface of Swift Premium Brown and Serve Sausages. Prior to microwaving the treated and untreated sausages were not distinguishable by visual inspection. The treated sausages and untreated sausages (which were used as a control) were microwaved for two minutes. After microwaving, sausages treated with the 12° Brix browning composition had a rich golden brown color compared to the untreated control sausages which had a grayish white color. There was no palatable difference in terms of flavor between the two groups of sausages. This shows that the flavorless browning composition browned the sausages without also contributing a detectable flavor to the sausages.

EXAMPLE 5

This example describes a method for producing a high browning, flavorless aqueous composition from lactose.

Lactose was pyrolyzed at 500° C. in an upflow circulating fluidized bed reactor described in connection with FIG. 4. The reactor was capable of processing about 100 lbs/hr of solid feedstock. The vapor residence time in the reactor was about 0.7 second, the pressure was about 1-1.5 psi and the pyrolysis product was condensed by direct contact with circulating 20° C. water, as described in Example 1. The resulting pyrolysis liquid contained about 2° Brix total organic solids as determined by refractive index. The HAA concentration was 0.11%, the acetic acid content was less than about 0.01% and the acetol content was about 0.06%, as determined by analytical gas chromatography. The pyrolysis liquid then was concentrated by evaporation at 50° C. under a vacuum of −29 inches mercury to provide a concentrated pyrolysis liquid containing 26° Brix organic solids including 4% wt/vol HAA. The concentrated pyrolysis liquid (60 ml) was extracted with three individual portions of food grade methylene chloride (20 ml) to remove flavor components such as furfural, phenolics and pyrazines. The extracted pyrolysis liquid then was concentrated to 50° Brix organic solids to remove low molecular weight flavor components. This concentrated and extracted pyrolysis liquid contained 11% wt/vol HAA. The concentrated pyrolysis liquid then was diluted with water back to 5% wt/vol HAA and 19° Brix organic solids.

This diluted, high browning and flavorless aqueous composition was applied to the surface of Swift Premium Brown and Serve Sausages by dipping the sausages into the composition for two to three seconds and then allowing the sausages to drip dry for thirty seconds. The treated sausages and untreated sausages (which were used as a control) were microwaved. Prior to microwaving, the treated and untreated sausages were not distinguishable-by visual inspection. After microwaving, sausages treated with the 19° Brix browning composition had a rich golden brown color compared to the untreated control sausages which had a grayish white color. There was no palatable difference in terms of flavor between the two groups of sausages. This shows that the flavorless browning composition browned the sausages without also contributing a detectable flavor to the sausages.

EXAMPLE 6

This example shows a second method for producing a high browning, flavorless aqueous composition by the pyrolysis of dextrose, and the usefulness of the composition in browning a foodstuff cooked in a microwave oven.

Dextrose was pyrolyzed according to the method of Example 4 and the resulting pyrolysis liquid was concentrated to 18° Brix organic solids and 6% wt/vol HAA. A portion of concentrated pyrolysis liquid (60) then was treated batchwise with two types of food grade resins, first with Rohm and Haas nonionic XAD-4 resin (6 grams) and then with Rohm and Haas cationic IR-120 resin (3 grams) to remove flavor components. The pyrolysis liquid, after resin treatment, contained about 13° Brix organic solids by refractive index. The resulting pyrolysis liquid then was concentrated to about 50° Brix organic solids by evaporation to remove low molecular weight flavor components. Gas chromatographic analysis showed that this concentrated pyrolysis liquid contained 23% wt/vol HAA and that furfural, phenolics and pyrazines were the major flavor constituents removed by the resin treatment and evaporation. The concentrated pyrolysis liquid then was diluted with water back to 5% wt/vol HAA and about 12° Brix organic solids.

This diluted, high browning and flavorless aqueous composition was applied to the surface of Swift Premium Brown and Serve Sausages. The sausages and untreated sausages (which were used as a control) were microwaved. Prior to microwaving, the treated and untreated sausages were not distinguishable by visual inspection. After microwaving, sausages treated with the 12° Brix browning composition had a rich golden brown color compared to the control sausages which had a grayish white color. There was no palatable difference in terms of flavor between the two groups of sausages. This shows that the flavorless browning composition browned the sausages without also contributing a detectable flavor to the sausages.

EXAMPLE 7

This example describes removing undesirable flavor components from a pyrolysis liquid derived from lactose by methylene chloride extraction.

Lactose was fast pyrolyzed according to the method of Example 5. The resulting aqueous pyrolysis liquid was found to contain about 2° Brix total organic solids by refractive index. This pyrolysis liquid was concentrated by evaporation at 50° C. and −29 inches of mercury to about 26° Brix organic solids, and then divided into two portions. One portion (100 ml) was extracted with food grade methylene chloride (3×30 ml) and the second portion was not extracted (to serve as a control). The organic solids in the extracted portion dropped from 26° Brix to 22° Brix.

Each portion then was diluted to 150 ppm organic solids with distilled water. A triangular taste panel was set up with the following three samples:
A=Extracted Diluted Sample
B=Not Extracted Diluted Sample
C=Not Extracted Diluted Sample
Ten taste panelists were asked to pick the odd sample and comment on the flavors. Seven of the panelists identified Sample A as the odd sample. Comments of the panelists indicated Sample A had virtually no flavor compared to B and C, which each had a mild smoky flavor. This demonstrates that methylene chloride extraction is an effective way to remove flavor components from the pyrolysis liquid derived from lactose.

EXAMPLE 8

This example describes a method of producing a pyrolysis liquid from starch.

A sample of FRO-DEX-24-D (Amaizo Co., Hammond, Ind.), a powdered starch containing 6% moisture and having a 26% dextrose equivalent content was fast pyrolyzed at about 550° C. in an upflow circulating fluidized bed reactor such as illustrated in FIG. 4. The vapor residence time was about 200 msec and the pyrolysis product was condensed and solubilized using a cold water condenser. The resulting pyrolysis liquid contained about 51° Brix organic solids by refractive index and 24% wt/vol HAA by gas chromatography. Thus, the HAA concentration was about 50% of the organic solids of the condensed pyrolysis liquid.

EXAMPLE 9

This example describes another method of producing a pyrolysis liquid from starch.

A sample of PF powdered starch (Amaizo Co., Hammond, Ind.) containing about 12% moisture was fast pyrolyzed at about 550° C. in an upflow circulating fluidized bed reactor. The vapor residence time was about 200 msec and the pyrolysis product was condensed and solubilized using a cold water condenser. The resulting pyrolysis liquid contained 56° Brix organic solids by refractive index and 29% wt/vol HAA by gas chromatography. Thus, the HAA concentration was about 50% of the organic solids of the pyrolysis liquid.

EXAMPLE 10

This example describes a method of producing a high browning, flavorless aqueous composition from corn syrup.

High dextrose corn syrup having 83.7% total solids and 16.3% moisture (62 D.E./44 Baume' corn syrup, ADM Corn Sweetners, Cedar Rapids, Iowa) was heated to about 150° F. and then pumped through steam heated conduits into an upflow circulating fluidized bed reactor illustrated in FIG. 4. The heated corn syrup entered the reactor through a nozzle having a 3/32 inch aperture. The reactor temperature was about 550° C., the vapor residence tim was about 700 msec and the pressure was about 1.5 psi. The pyrolysis product was condensed and solubilized by direct contact with 20° C. recirculating water to give a pyrolysis liquid having about 30° Brix. The composition of the pyrolysis liquid was:

| | |
|---|---|
| Hydroxyacetaldehyde | 16.1% |
| Acetol | 0.81% |
| Acetic Acid | 1.6% |
| Cyclotene | 0.06% |
| Furfural | 0.41% |
| Methanol/Methyl Acetate | 0.83% |
| Maltol | 0.10% |
| Formic Acid | <0.1% |

The 30° Brix pyrolysis liquid was extracted with methylene chloride (one volume methylene chloride to ten volumes solution), and then the resulting pyrolysis liquid was concentrated by evaporation under reduced pressure (−28.5 inches of mercury) at about 50° C. to give a high browning, flavorless aqueous composition of about 45° Brix.

EXAMPLE 11

The corn syrup-derived pyrolysis liquid of Example 10 was diluted with water to about 23° Brix and compared to four different liquid pyrolysis samples: 1) a methylene chloride-extracted, slow pyrolysis liquid smoke, which is commercially available and made according to the procedure described in Nicholson U.S. Pat. No. 4,717,576 (briefly CHARSOL C-12, 500 ml, 28° Brix, 12% titratable acidity, browning index 12, available from Red Arrow Products Company Inc., Manitowoc, Wis., was extracted with methylene chloride, 50 ml, to give a wood-derived liquid smoke of about 23° Brix); 2) a fast pyrolysis product of Avicel pH 101 cellulose made according to the procedure described in Example 8 of U.S. Pat. No. 5,039,537; 3) a fast pyrolysis product of maple sawdust made according to the procedure described in Example 6 of U.S. Pat. No. 5,039,537 and treated by contact with a XAD-4 nonionic resin; and 4) a fast pyrolysis product of dextrose the values were calculated from the data in Example 2, above, in direct proportion to ° Brix values.

Comparative physical properties of the five liquid products are illustrated in Table 3.

tions to food casings because casings are susceptible to degradation at low pH values.

The foregoing detailed description has been given for clearness of understanding only, and no unnecessary limitations should be understood therefrom, as modifications will be obvious to those skilled in the art.

What is claimed is:

1. A method of producing a browning liquid product for application to foodstuffs comprising the steps of:
    (a) pyrolyzing a feedstock selected from the group consisting of a sugar, a starch and mixtures thereof to produce a vaporous pyrolysis product and a pyrolytic residue, said vaporous pyrolysis product comprising condensable vapors and noncondensable vapors;
    (b) separating the vaporous pyrolysis product from the pyrolytic residue and unpyrolyzed feedstock;
    (c) condensing the condensable vapors in the vaporous pyrolysis product to produce a water-soluble pyrolysis liquid;
    (d) contacting the water-soluble pyrolysis liquid with a water-insoluble organic extraction solvent to extract flavoring materials from the water-soluble pyrolysis liquid into the water-insoluble organic extraction solvent; and
    (e) separating the water-insoluble organic extraction solvent from the so-extracted water-soluble pyrolysis liquid to yield the so-extracted water-soluble pyrolysis liquid as a browning liquid product which has substantially no detectable smoke flavoring ability by taste.

2. The method of claim 1 wherein the feedstock comprises dextrose.

3. The method of claim 1 wherein the feedstock comprises lactose.

4. The method of claim 1 wherein sufficient water is added to the water-soluble pyrolysis liquid produced in step (c) to provide a water-soluble pyrolysis liquid having a maximum specific gravity of about 30° Brix.

5. The method of claim 1 wherein the browning liquid product of step (e) is further contacted with a member of the group consisting of a cationic exchange resin, a nonionic exchange resin and mixtures thereof to further remove flavoring materials and produce a browning liquid product which is essentially flavorless but which browns a foodstuff.

TABLE 3

| Liquid | °Brix | Titratable Acidity | Browning Index | Titratable Acidity/ Browning Index (B.I.) | Casing Browning* Density B.I./cm² |
|---|---|---|---|---|---|
| CHARSOL C-12 (methylene chloride extracted) | 23 | 11.7 | 10.3 | 1.14 | 0.0151 |
| AVICEL pH 101 | 23 | 1.0 | 16.3 | 0.061 | 0.0239 |
| HARDWOOD (XAD-4 resin extracted) | 23 | 4.5 | 19.4 | 0.23 | 0.0284 |
| DEXTROSE | 23 | 1.0 | 47.6 | 0.021 | 0.0697 |
| CORN SYRUP (methylene chloride extracted from Example 10) | 23 | 1.6 | 53.0 | 0.030 | 0.0776 |

*Values calculated according to the procedures described by Nicholson U.S. Pat. No. 4,717,576

The above data indicate that the high browning, flavorless aqueous composition prepared according to Example 10 has a significantly higher casing browning density value compared to commercial liquid smoke treated by the method disclosed in Nicholson U.S. Pat. No. 4,717,576 (0.0776 to 0.0151). In addition, the pyrolysis of sugars and starches provides a pyrolysis liquid with a significantly reduced acidity. Such low acidity liquid products are particularly preferred for applica- 6. The method of claim 5 wherein the essentially flavorless browning liquid product is concentrated to raise its specific gravity.

7. The method of claim 6 wherein the essentially flavorless browning liquid product is concentrated to at least 40° Brix.

8. The method of claim 1 wherein the browning liquid product is concentrated.

9. The method of claim 8 wherein the browning liquid product then is diluted with water to provide a browning liquid product comprising at least 0.05% wt/vol of hydroxyacetaldehyde.

10. The method of claim 1 wherein the water-insoluble organic extraction solvent is one in which hydroxyacetaldehyde has very little solubility.

11. The method of claim 1 wherein the water-insoluble organic extraction solvent has a water solubility of 3 parts or less per 100 parts of water, by volume.

12. The method of claim 11 wherein the organic extraction solvent is selected from the group consisting of methylene chloride, chloroform, 1,1,1-trichloroethane, ethylene dichloride, carbon tetrachloride, and mixtures thereof.

13. The method of claim 1 wherein the vaporous pyrolysis product is condensed in step (c) by direct contact with a colder liquid.

14. The method of claim 13 wherein the colder liquid is water, the condensed water-soluble pyrolysis liquid, or a mixture thereof.

15. A method of browning a foodstuff without imparting strong smoke flavor to the foodstuff comprising:
   (a) applying the browning liquid product produced by the method of claim 1 to a foodstuff in a sufficient amount to develop an acceptable brown color in the foodstuff; then
   (b) heating the foodstuff at a sufficient temperature and for a sufficient time for the browning liquid product to brown the foodstuff.

16. The method of claim 15 wherein the foodstuff is an encased foodstuff.

17. The method of claim 15 wherein the foodstuff is bacon.

18. The method of claim 15 wherein the foodstuff is a sausage.

19. A liquid product for browning a cooked foodstuff, said liquid product prepared by the method of claim 1.

20. A high browning, flavorless aqueous composition derived from vapor of a pyrolyzed material selected from the group consisting of a sugar, a starch and mixtures thereof, wherein the material is pyrolyzed at about 400° C. to about 1000° C. and the composition has a soluble organic content of less than 50° Brix, a browning index greater than about 30, and ratio of titratable acidity to browning index of less than about 0.06.

21. The composition of claim 20 wherein the composition is derived from corn syrup and the composition has a titratable acidity of about 3.2%, a browning index of about 104 and a soluble organic content of about 45° Brix.

22. The composition of claim 20 wherein the browning index is greater than about 50.

23. The composition of claim 20 wherein the browning index is greater than about 75.

24. A high browning, flavorless aqueous composition derived from vapor of a pyrolyzed material selected from the group consisting of a sugar, a starch and mixtures thereof, wherein the material is pyrolyzed at about 400° C. to about 1000° C. and the composition has a casing browning density of greater than 0.03.

25. A method of producing a browning liquid product comprising the steps of:
   (a) pyrolyzing a feedstock selected from the group consisting of a sugar, a starch and mixtures thereof to produce a vaporous pyrolysis product and a pyrolytic residue, said vaporous pyrolysis product comprising condensable vapors and noncondensable vapors;
   (b) separating the vaporous pyrolysis product from the pyrolytic residue and unpyrolyzed feedstock;
   (c) condensing the condensable vapors in the vaporous pyrolysis product to produce a water-soluble pyrolysis liquid; and
   (d) contacting the water-soluble pyrolysis liquid with a member of the group consisting of an cationic exchange resin, a nonionic exchange resin and mixtures thereof to remove flavoring materials and thereby produce a browning liquid product which has no detectable smoke flavoring ability by taste.

26. The method of claim 25 wherein the feedstock comprises dextrose, lactose or a mixture thereof.

27. The method of claim 25 wherein sufficient water is added to the water-soluble pyrolysis liquid produced in step (c) to provide a water-soluble pyrolysis liquid having a maximum specific gravity of about 30° Brix.

28. The method of claim 25 wherein the browning liquid product is concentrated to raise its specific gravity.

29. The method of claim 28 wherein the browning liquid product is concentrated to at least 40° Brix.

30. The method of claim 28 wherein the browning liquid product then is diluted with water to provide a browning liquid product comprising at least 0.05% wt/vol of hydroxyacetaldehyde.

31. The method of claim 25 further comprising the steps of:
   (e) contacting the browning liquid product produced in step (d) with a water-insoluble organic extraction solvent to further extract flavoring materials from the browning liquid product into the water-insoluble organic extraction solvent; and
   (f) separating the water-insoluble organic extraction solvent from the so-extracted browning liquid product and produce a browning liquid product which is essentially flavorless but which browns a foodstuff.

* * * * *

UNITED STATES PATENT AND TRADEMARK OFFICE
CERTIFICATE OF CORRECTION

PATENT NO. : 5,397,582
DATED : March 14, 1995
INVENTOR(S) : Gary L. Underwood, et al It is certified that error appears in the above-indentified patent and that said Letters Patent is hereby corrected as shown below:

Column 2, lines 54, 55, "the a" should be --the--

Column 11, lines 20-21, "and is fed and is to primary cyclone separator 49" should be --and is fed to primary cyclone separator 49--

Column 12, line 14, "and a is fed" should be --and is fed--

Column 15, line 31, "(60)" should be --(60 ml)--

Column 16, last line, "tim" should be --time--

Signed and Sealed this

Twenty-fourth Day of October, 1995

Attest:

BRUCE LEHMAN

Attesting Officer

Commissioner of Patents and Trademarks